United States Patent [19]

Wermuth et al.

[11] Patent Number: 5,254,548
[45] Date of Patent: Oct. 19, 1993

[54] COMPOUNDS HAVING AN ARYLTRIAZINE STRUCTURE

[75] Inventors: Camille-Georges Wermuth, Strasbourg; Jean-Jacques Bourguignon, Hipsheim; Isabelle Morin, Le Raincy; Pierre Renard, Versailles; Michelle Devissaguet, Neuilly sur Seine; Jean-Francois R. de La Faverie, Le Chesnay; Gérard Adam, Le Mesnil le Roi, all of France

[73] Assignee: Adir et Compagnie, Courbevoie, France

[21] Appl. No.: 820,512

[22] Filed: Jan. 14, 1992

[30] Foreign Application Priority Data

Jan. 15, 1991 [FR] France ................. 91 00338

[51] Int. Cl.⁵ ............... A61K 31/53; C07D 253/065
[52] U.S. Cl. ......................... 514/242; 514/231.2; 544/60; 544/88; 544/111; 544/182
[58] Field of Search ............... 544/182, 53, 60, 88, 544/111; 514/242

[56] References Cited

FOREIGN PATENT DOCUMENTS 0169139 1/1986 European Pat. Off. ............ 544/182

Primary Examiner—Mukund J. Shah
Assistant Examiner—Y. N. Gupta
Attorney, Agent, or Firm—Gordon W. Hueschen

[57] ABSTRACT

A compound having an aryltriazine structure selected from those of formula (I):

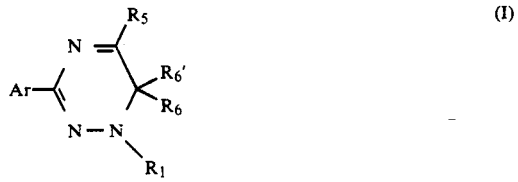

for which the meaning of the substituents Ar, $R_1$, $R_5$, $R_6$, and $R_6'$ is given in the description.

The compound of the invention is useful as medicinal product for disorders associated with a cholinergic dysfunction.

9 Claims, No Drawings

COMPOUNDS HAVING AN ARYLTRIAZINE STRUCTURE

The invention relates to new compounds having an aryltriazine structure.

Compounds having an aryltriazine structure are known from the literature, especially 1,2,4-aryltriazine-6-ones which have been mentioned as herbicides, and aryltriazolo[3,4-f][1,2,4]triazines the pharmacological activities of which have not been researched. The Applicant has now discovered new aryltriazine compounds that, very interestingly, possess analgesic properties and acetylcholine esterase-inhibiting properties, as well as significant affinities for certain central receptors, and in this capacity they can usefully be used in human medicine. The closest prior art to the compounds of the invention is presented by the following documents: Hétérocycles, (1989), 29 (12), 2279-2285; U.S. Pat. No. 4,362,550; Chem. Abstracts 105: 172410; EP 169 139.

The invention relates more specifically to compounds having an aryltriazine structure corresponding to the general formula I:

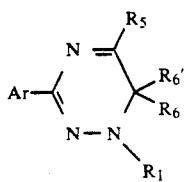 (I)

in which:

Ar represents an optionally substituted aryl or heteroaryl radical, $R_5$ represents a hydrogen atom, an alkyl, cycloalkyl, or cycloalkylalkyl radical, or an aryl, aralkyl, heteroaryl, or heteroaralkyl radical each of which is optionally substituted in the aromatic or hetero-aromatic ring, and either:

$R_6$ and $R_6'$ together with the carbon atom carrying them represent a C=O function, and $R_1$ represents a chain

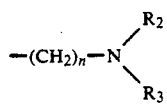

in which:

n represents 2, 3, or 4, $R_2$ and $R_3$, which are the same or different, each represents a hydrogen atom or an alkyl radical or, together with the nitrogen atom carrying them, a heterocycle selected from morpholine, pyrrolidine, piperidine, perhydroazepine, and piperazine optionally substituted at the other nitrogen atom by an alkyl chain or by an optionally substituted phenyl radical, or:

$R_1$ and $R_6$ together form a bond, and $R_6'$ represents a radical of the formula:

in which $R_7$ represents a hydrogen atom or an alkyl radical, and $R_8$ represents a group of the formula:

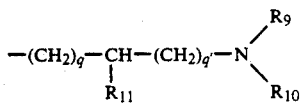

in which q represents an integer of from 1 to 3, q' represents 0 or 1, $R_9$, $R_{10}$, and $R_{11}$ each represents, independently of the others, a hydrogen atom, or an alkyl radical, or $R_9$ and $R_{10}$ together with the nitrogen atom carrying them form a mono- or bi-cyclic heterocycle having from 5 to 10 apices that is saturated or contains a double bond and optionally includes in its skeleton an additional hetero atom selected from nitrogen, oxygen, and sulphur, it being understood that, when $R_9$ and $R_{10}$ together form a heterocycle containing a second nitrogen atom, that nitrogen atom may itself be substituted by an optionally substituted alkyl, aryl, or heteroaryl radical, or by a chain of the formula

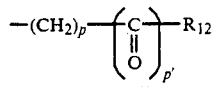

in which p represents 1, 2, or 3, p' represents 0 or 1, and $R_{12}$ represents an optionally substituted aryl or heteroaryl radical, or $R_9$ and $R_{11}$ together with the nitrogen and carbon atoms carrying them form a heterocycle having from 5 to 7 apices that optionally includes in its skeleton an additional hetero atom selected from nitrogen, oxygen, and sulphur, or $R_7$ and $R_8$ together with the nitrogen atom carrying them form a piperazine substituted at the other nitrogen atom by an alkyl radical, by an optionally substituted phenyl radical, or by a chain of the formula

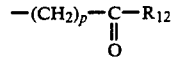

in which p and $R_{12}$ are as defined above, or:

$R_1$, $R_6$, and $R_6'$, together with the triazine nucleus carrying them, form a [1,2,4-triazolo][3,4-f][1,2,4]-triazine system, the triazole nucleus being substituted at the 3 position by an $R_{13}$ group selected from an alkyl radical, and an aryl, heteroaryl, aralkyl, and heteroaralkyl radical each of which is optionally substituted in the aromatic or heteroaromatic ring, their possible optical isomers, isolated or in the form of a mixture, as well as, where applicable, their addition salts with a pharmaceutically acceptable acid, it being understood that :

the term "substituted" indicates that the groups it governs may be substituted by one or more identical or different radicals selected from halogen, hydroxy, nitro, amino, trifluoromethyl, alkyl, and alkoxy, and/or may carry at two adjacent carbon atoms an —O—(CH$_2$)$_r$—O— group in which r represents an integer of from 1 to 3, unless indicated otherwise, the terms "alkyl" and "alkoxy" indicate groups containing from 1 to 6 carbon atoms in a straight or branched chain, and the term "cycloalkyl" denotes a saturated cyclic group containing from 3 to 7 carbon atoms, the term "aryl" indicates a phenyl or naphthyl group, and the term "heteroaryl" denotes a mono- or bi-cyclic aromatic group having from 5 to 10 apices that includes in its carbon skeleton from 1 to 3 hetero atoms selected from nitrogen, oxygen and sulphur.

A process for the preparation of the compounds of formula I is described wherein an α-amino acid of formula II

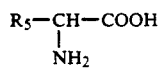 (II)

in which R$_5$ has the same meaning as in formula I, is condensed in alkaline medium with an acid halide of the formula Ar · COX, in which Ar has the same meaning as in formula I and X represents a halogen atom, to yield a compound of formula III

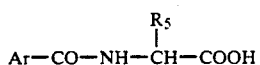 (III)

in which Ar and R$_5$ have the meanings given above, which is then:

a) either esterified in acidic medium with a lower alcohol of the formula R'—OH in which R' represents a lower alkyl radical, to yield a compound of formula IVa

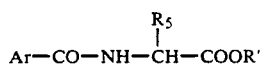 (IVa)

in which Ar, R$_5$, and R' have the meanings given above, which is subjected in anhydrous medium to the action of a thionating reagent, such as phosphorus pentasulphide or Lawesson's reagent, followed by acidification of acid-base extraction, to yield a compound of formula Va

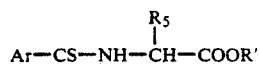 (Va)

in which Ar, R$_5$, and R' have the meanings given above, or subjected to the action of a trialkyloxonium tetrafluoroborate, in an anhydrous solvent, to yield a compound of formula Vb

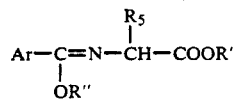 (Vb)

in which Ar, R$_5$, and R' have the meanings given above and R" represents an alkyl group.

the compound of formula Va or Vb then being cyclised by the action of hydrazine at elevated temperature in an aprotic solvent to form a compound of formula VI

 (VI)

in which Ar and R$_5$ have the meanings given above, which is then dehydrogenated, either by dehydrohalogenation or by the action of an oxidising reagent, such as, for example, potassium permanganate, manganese dioxide, sodium meta-nitrobenzenesulphonate, or sodium perchlorate, to form a compound of formula VII

 (VII)

in which Ar and R$_5$ have the meanings given above, which is then:

either treated in succession with an alkali metal alcoholate and then an aminoalkyl halide of formula VIII

 (VIII)

in which n, R$_2$, and R$_3$ have the same meaning as in formula I and X represents a halogen atom, to yield a compound of formula Ia

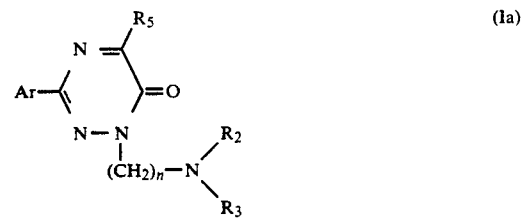 (Ia)

a particular case of compounds of formula I, or subjected to the action of a polyhalogenated phosphorus compound to yield a compound of formula IX

 (IX)

in which Ar, R$_5$, and X have the meanings given above, which is either condensed with an amine of formula X

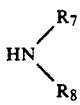

in which $R_7$ and $R_8$ have the same meaning as in formula I, to yield a compound of formula Ib

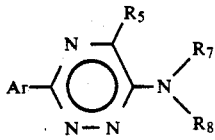 (Ib)

a particular case of compounds of formula I, or alternatively condensed with a hydrazide of formula

 (XI)

in which $R_{13}$ has the same meaning as in formula I, to yield a compound of formula Ic

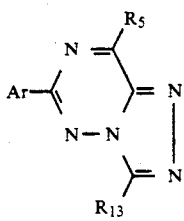 (Ic)

a particular case of compounds of formula I, it being possible, if desired, for the compound Ia, Ib, and Ic, which form the totality of the compounds of formula I, to be converted into salts by the addition of a pharmaceutically acceptable acid and, where applicable, separated into their optical isomers, b) or, optionally, when $R_5$ represents a hydrogen atom, condensed in acetic anhydride, in the presence of an alkali metal acetate, with an aromatic aldehyde of formula $Ar_1$-CHO, in which $Ar_1$ represents an optionally substituted aryl or heteroaryl radical, to yield a compound of formula Vc

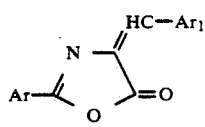 (Vc)

in which Ar and $Ar_1$ have the meanings given above, which is subjected to the action of hydrazine to obtain a compound of formula Vd

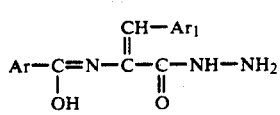 (Vd)

in which Ar and $Ar_1$ have the meanings given above, which is heated in an alkaline medium to yield a compound of formula VIIa

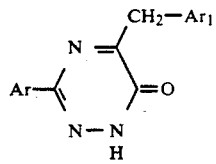 (VIIa)

a particular case of compounds of formula VII in which $R_5$ represents an optionally substituted arylmethyl or heteroarylmethyl radical, which is subjected to the same operations as the compounds of the general formula VII to obtain, respectively, the compounds of formula Ia', Ib', and Ic'

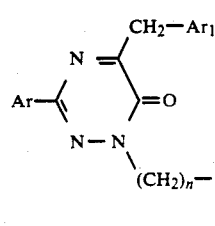 (Ia')

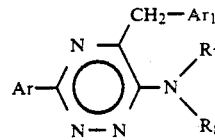 (Ib')

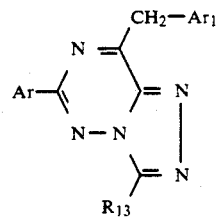 (Ic')

particular cases of compounds of formula Ia, Ib and Ic, which, if desired, are converted into salts by the addition of a pharmaceutically acceptable acid and, where applicable, separated into their optical isomers.

The compounds of formula I have valuable pharmacological properties.

In vitro binding tests have shown that the compounds have a good affinity for $A_1$, $A_2$, $M_1$, and sigma receptors. Moreover, they exhibit a pronounced acetylcholine esterase-inhibiting activity.

Tests carried out in vivo show that the substances are non-toxic at the doses tested and also have an analgesic activity.

The compounds of the invention can therefore be used for the treatment of pain, cognitive disorders that may or may not be associated with ageing, depression, anxiety and psychoses, sleeping disorders, epilepsy, arterial hypertension, cardiac insufficiency or cardiac arrhythmia, cardiac or cerebral ischaemia, blood hypercoagulability and thromboses, asthma, renal deficiency and, generally, disorders associated with $A_1$, $A_2$, or sigma receptor dysfunction, or with cholinergic system dysfunction.

The present invention also relates to pharmaceutical compositions comprising as active ingredient at least one compound of the general formula (I) or an addition salt thereof with a pharmaceutically acceptable acid, alone or in combination with one or more excipients or vehicles.

Among the pharmaceutical compositions according to the invention there may be mentioned more especially those suitable for oral, parenteral, or nasal administration, tablets, dragees, sublingual tablets, sachets, paquets, capsules, glossettes, lozenges, suppositories, creams, ointments, dermal gels, injectable solutions, etc.

The dosage used varies in accordance with the age and weight of the patient, the nature and severity of the disorder and the administration route, which may be oral, nasal, rectal, intramuscular, or parenteral.

Generally, the unit dosage ranges from 1 to 500 mg for a treatment 1 to 3 times per 24 hours.

The following Examples illustrate the invention but do not limit it in any way.

The starting materials are described in the literature or may be prepared in an identical manner.

EXAMPLE 1:
1-MORPHOLINOETHYL-5-ISOPROPYL-3-PHENYL-1,2,4-TRIAZIN-6-ONE

Step A: N-Benzoylvaline

Dissolve 0.1 mol (11.7 g) of valine in 50 ml of water, add 0.25 mol of sodium hydroxide in aqueous solution, heat to 30° C. and then add dropwise 0.15 mol (17.5 ml) of benzoyl chloride. Wash the aqueous solution with ether, acidify and suction off the N-benzoylvaline crystals.

Melting point: 125° C.
Yield: 95%

Step B: Ethyl N-Benzoylvalinate

Dissolve in 100 ml of ethanol 0.045 mol (10 g) of N-benzoylvaline obtained in the preceding Step, add 5 ml of concentrated sulphuric acid, then heat at reflux for 24 hours. Evaporate to dryness, take up in ether, wash with water then with a 10% potassium bicarbonate solution, dry, filter and evaporate to dryness. Ethyl N-benzoylvalinate is obtained.

Yield: 71%
Melting point: 74° C.

Stage C: Ethyl N-Thiobenzoylvalinate

Heat at reflux for 6 hours a solution of 0.025 mol (6.3 g) of ethyl N-benzoylvalinate obtained in Step B and 5.6 g of phosphorus pentasulphide in 120 ml of pyridine, and evaporate to dryness. Take up the residue in water and ethyl acetate. Wash the organic phase with a 2N hydrochloric acid solution, dry, filter and evaporate to dryness. The ethyl N-thiobenzoylvalinate obtained is purified by chromatography on a column of silica (eluant:ethyl acetate/hexane:25/75).

Yield: 45% (yellow oil)

Step D:
4,5-dihydro-3-phenyl-5-isopropyl-1,2,4-triazine-6-one

Dissolve in 25 ml of xylene 0.01 mol (2.85 g) of ethyl N-thiobenzoylvalinate obtained in Step C. Add 0.02 mol of hydrazine hydrate. Reflux for 12 hours. Suction off the resulting precipitate and wash it with acetone.

4,5-dihydro-3-phenyl-5-isopropyl-1,2,4-triazin-6-one is obtained Yield: 61% Melting point: 164° C.

Step E: 3-phenyl-5-isopropyl-1,2,4-triazine-6-one

Dissolve in 400 ml of acetone 0.01 mol (2.15 g) of the compound obtained in the preceding Step. Add 8 grams of potassium permanganate dissolved in 400 ml of water, and reflux for 4 hours. Filter, evaporate to dryness and recrystallise the 3-phenyl-5-isopropyl-1,2,4-triazin-6-one from methanol.

Yield: 50% Melting point: 188° C.

Step F:
1-morpholinoethyl-5-isopropyl-3-phenyl-1,2,4-triazin-6-one (Acid Oxalate)

Add 5 mmol of sodium ethoxide, then a solution of 4.6 mmol of N-(2-chloroethyl)morpholine hydrochloride and 5 mmol of sodium ethoxide in ethanol to a solution in ethanol of 4.6 mmol (1 gram) of the compound obtained in the preceding Step. Heat at reflux for 6 hours, and filter off the sodium chloride formed. Evaporate the filtrate to dryness, take up in water and extract with ethyl acetate. Concentrate to dryness, and dissolve the residue in isopropanol at elevated temperature Add one equivalent of oxalic acid. The acid oxalate of 1-morpholinoethyl-5-isopropyl-3-phenyl-1,2,4-triazin-6-one precipitates.

Yield: 68%
Melting point: 210° C.

| Percentage analysis: | C % | H % | N % |
| --- | --- | --- | --- |
| calculated | 57.40 | 6.26 | 13.39 |
| found | 57.46 | 6.33 | 13.24 |

EXAMPLE 2:
1-MORPHOLINOETHYL-5-ISOPROPYL-3-(2-CHLOROPHENYL)-1,2,4-TRIAZIN-6-ONE

By replacing the benzoyl chloride in Step A of Example 1 with 2-chlorobenzoic acid chloride there are obtained in succession, in the same manner:

Step A: N-(2-chlorobenzoyl)valine

Yield: 78%
Melting point: 89° C.

Step B: Ethyl N-(2-chlorobenzoyl)valinate

Yield: 76% (oil)

Step C: Ethyl N-(2-chlorothiobenzoyl)valinate

Yield: 50% (yellow oil)

Step D:
4,5-Dihydro-3-(2-chlorophenyl)-5-isopropyl-1,2,4-triazin-6-one

Yield: 66%
Melting point: 98° C.

Step E:
3-(2-chlorophenyl)-5-isopropyl-1,2,4-triazin-6-one

Yield: 56%
Melting point: 118.5° C.

Step F:
1-morpholinoethyl-3-(2-chlorophenyl)-5-isopropyl-1,2,4-triazin-6-one in acid oxalate form Yield: 50%
Melting point: 188° C.

| Percentage analysis: | C % | H % | N % |
| --- | --- | --- | --- |
| calculated | 53.03 | 5.56 | 12.37 |

-continued

| Percentage analysis: | C % | H % | N % |
|---|---|---|---|
| found | 52.97 | 5.64 | 12.27 |

EXAMPLE 3:
1-(3-MORPHOLINOPROPYL)-3-(2-CHLOROPHENYL)-5-ISOPROPYL-1,2,4-TRIAZIN-6-ONE

By replacing the 2-chloroethylmorpholine in Step F of Example 2 with N-(3-chloropropyl)morpholine, the product of the Example is obtained in the form of the oxalate.

Melting point: 172° C.

EXAMPLE 4:
1-PYRROLIDINOETHYL-3-(2-CHLOROPHENYL)-5-ISOPROPYL-1,2,4-TRIAZIN-6-ONE

By replacing the N-(3-chloropropyl)morpholine in the preceding Example with N-(2-chloroethyl)pyrrolidine, the compound of the Example is obtained in the form of the acid oxalate.

Melting point: 179° C.

EXAMPLES 5 TO 8

By proceeding as in the preceding Examples, but using an appropriate haloalkylamine, the following compounds are obtained in the same manner in the form of oxalates:

EXAMPLE 5: 1-(4-MORPHOLINOBUTYL)-3-(2-CHLOROPHENYL)-5-ISOPROPYL-1,2,4-TRIAZIN-6-ONE

EXAMPLE 6: 1-[(4-METHYL-1-PIPERAZINYL)ETHYL]-3-(2-CHLOROPHENYL)-5-ISOPROPYL-1,2,4-TRIAZIN-6-ONE

EXAMPLE 7: 1-[[4-(3-TRIFLUOROMETHYLPHENYL)-1-PIPERAZINYL]ETHYL]-3-(2-CHLOROPHENYL)-5-ISOPROPYL-1,2,4-TRIAZIN-6-ONE

EXAMPLE 8: 1-DIETHYLAMINOETHYL-3-(2-CHLOROPHENYL)-5-ISOPROPYL-1,2,4-TRIAZIN-6-ONE

EXAMPLE 9: 1-MORPHOLINOETHYL-3-(3-METHOXYPHENYL)-5-ISOPROPYL-1,2,4-TRIAZIN-6-ONE

By replacing the benzoyl chloride in Step A of Example 1 with 3-methoxybenzoic acid chloride and proceeding in the same manner, the product of the Example is obtained in the form of the acid oxalate.

Melting point: 117° C.

EXAMPLE 10:
1-MORPHOLINOETHYL-3-(4-CHLOROPHENYL)-5-ISOPROPYL-1,2,4-TRIAZIN-6-ONE

By replacing the 3-methoxybenzoic acid chloride in the preceding Example with 4-chlorobenzoic acid chloride, the compound of the Example is obtained in the form of the acid oxalate.

Melting point: 213° C.

EXAMPLE 11:
1-MORPHOLINOETHYL-3-(3-CHLOROPHENYL)-5-ISOPROPYL-1,2,4-TRIAZIN-6-ONE

By replacing the 4-chlorobenzoic acid chloride in the preceding Example with 3-chlorobenzoic acid chloride, the compound of the Example is obtained in the form of the acid oxalate.

Melting point: 211° C.

EXAMPLE 12:
1-MORPHOLINOETHYL-3-PHENYL-5-METHYL-1,2,4-TRIAZIN-6-ONE

By replacing the valine in Step A of Example 1 with alanine there are obtained in succession:

N-BENZOYLALANINE (melting point: 98.5° C.)

ETHYL N-BENZOYLALANINATE (melting point: 70° C.)

ETHYL N-THIOBENZOYLALANINATE (melting point: 119° C.)

4,5-DIHYDRO-3-PHENYL-5-METHYL-1,2,4-TRIAZIN-6-ONE (melting point: 177° C.)

3-PHENYL-5-METHYL-1,2,4-TRIAZIN-6-ONE (melting point: 230° C.)

1-MORPHOLINOETHYL-3-PHENYL-5-METHYL-1,2,4-TRIAZIN-6-ONE (melting point: 75°-76° C. in the form of a base)

EXAMPLE 13:
1-MORPHOLINOETHYL-3-(3-CHLOROPHENYL)-5-METHYL-1,2,4-TRIAZIN-6-ONE

By replacing the benzoyl chloride in the preceding Example with 3-chlorobenzoyl chloride, the product of the Example is obtained in the same manner in the form of the acid oxalate.

Melting point: 209° C.

EXAMPLE 14: 1-MORPHOLINOETHYL-3-(4 CHLOROPHENYL)-5-METHYL-1,2,4-TRIAZIN-6-ONE

By replacing in Example 1 the benzoyl chloride with 4-chlorobenzoyl chloride and the valine by alanine, there are obtained in succession:

Step A: N-(4-chlorobenzoyl)analine

Melting point: 178° C.

Step B: Ethyl N-(4-chlorobenzoyl)alaninate

Melting point: 88° C.

Step C: Ethyl N-[(4-chlorobenzoyl)ethoxymethylidene]alaninate

Add a solution of 0.1 mol (18.9 g) of triethyloxonium tetrafluoroborate in dichloromethane to a solution in dichloromethane of 0.05 mol (13 g) of ethyl N-(4-chlorobenzoyl)alaninate obtained in the preceding Step. Stir for 12 hours under an inert atmosphere. Wash the organic solution with a solution of potassium carbonate. Dry and evaporate the organic phase.

A yellow oil is obtained which is used directly as such in the following Step.

Step D: 4,5-dihydro-3-(4-chlorophenyl)-5-methyl-1,2,4-triazine-6-one

Add 0.012 mol of hydrazine hydrate to an ethanolic solution of 0.01 mol of the product obtained in the preceding Step. Heat at reflux for 6 hours, evaporate to dryness. Take up in water, suction off, dry and recrystallise from methanol.

Melting point: 144° C.

Steps E and F:

By operating as in Steps E and F of Example 1, using the product obtained in the preceding Step as starting material, there are obtained in the same manner 3-(4-CHLOROPHENYL)-5-METHYL-1,2,4-TRIAZIN-6-ONE

1-MORPHOLINOETHYL-3-(4-CHLOROPHENYL)-5-METHYL-1,2,4-TRIAZIN-6-ONE melting point: 109.5° C. (base)

EXAMPLE 15: 3-(2-CHLOROPHENYL)-5-ISOBUTYL-1-MORPHOLINOETHYL-1,2,4-TRIAZIN-6-ONE

By replacing the 4-chlorobenzoyl chloride with 2-chlorobenzoyl chloride and the alanine with leucine in Step A of the preceding Example, there are obtained in succession:

N-(2-CHLOROBENZOYL)LEUCINE
Melting point: 73° C.
ETHYL N-(2-CHLOROBENZOYL)LEUCINATE (oil)
ETHYL N-[(2-CHLOROPHENYL)-ETHOXYMETHYLIDENE]LEUCINATE
4,5-DIHYDRO-3-(2-CHLOROPHENYL)-5-ISOBUTYL-1,2,4-TRIAZIN-6-ONE
Melting point: 113° C.
3-(2-CHLOROPHENYL)-5-ISOBUTYL-1,2,4-TRIAZIN-6-ONE (oil)
1-MORPHOLINOETHYL-3-(2-CHLOROPHENYL)-5-ISOBUTYL-1,2,4-TRIAZIN-6-ONE in the form of the acid oxalate
Melting point: 175° C.

EXAMPLES 16 TO 21

By replacing the alanine in Step A of Example 14 with an appropriate amino acid, the following are obtained in the same manner:

EXAMPLE 16: 1-MORPHOLINOETHYL-3-(2-CHLOROPHENYL)-5-ETHYL-1,2,4-TRIAZIN-6-ONE

EXAMPLE 17: 1-MORPHOLINOETHYL-2-CHLOROPHENYL)-5-ALLYL-1,2,4-TRIAZIN-6-ONE

EXAMPLE 18: 1-MORPHOLINOETHYL-3-(2-CHLOROPHENYL)-5-(2-THIENYL)-1,2,4-TRIAZIN-6-ONE

EXAMPLE 19: 1-MORPHOLINOETHYL-3-(2-CHLOROPHENYL)-5-HEXYL-1,2,4-TRIAZIN-6-ONE

EXAMPLE 20: 1-MORPHOLINOETHYL-3-(2-CHLOROPHENYL)-5-(2-PHENYLETHYL)-1,2,4-TRIAZIN-6-ONE

EXAMPLE 21: 1-MORPHOLINOETHYL-3-(2-CHLOROPHENYL)-1,2,4-TRIAZIN-6-ONE

EXAMPLES 22 TO 27

By replacing the benzoyl chloride in Step A of Example 1 with the appropriate acid chloride, the following are obtained in the same manner:

EXAMPLE 22: 1-MORPHOLINOETHYL-3-(1-NAPHTHYL)-5-ISOPROPYL-1,2,4-TRIAZIN-6-ONE

EXAMPLE 23: 1-MORPHOLINOETHYL-3-(3-PYRIDYL)-5-ISOPROPYL-1,2,4-TRIAZIN-6-ONE

EXAMPLE 24: 1-MORPHOLINOETHYL-3-(2-THIENYL)-5-ISOPROPYL-1,2,4-TRIAZIN-6-ONE

EXAMPLE 25: 1-MORPHOLINOETHYL-3-(2-FURYL)-5-ISOPROPYL-1,2,4-TRIAZIN-6-ONE

EXAMPLE 26: 1-MORPHOLINOETHYL-3-(3,4-METHYLENEDIOXYPHENYL)-5-ISOPROPYL-1,2,4-TRIAZIN-6-ONE

EXAMPLE 27: 1-MORPHOLINOETHYL-3-(3,4-ETHYLENEDIOXYPHENYL)-5-ISOPROPYL-1,2,4-TRIAZIN-6-ONE

EXAMPLE 28: 1-MORPHOLINOETHYL-3-PHENYL-5-BENZYL-1,2,4-TRIAZIN-6-ONE

Step A: 2-phenyl-4-benzylidene-5-oxazolinone

Suspend 0.46 mol (38 g) of sodium acetate and 0.26 mol (26.4 ml) of benzaldehyde in 100 ml of acetic anhydride, heat to 65° C., add 0.32 mol (59 g) of hippuric acid and then heat at 90° C. for 30 minutes. Add 200 ml of hot water (80° C.) over a period of 10 minutes. Continue stirring for 10 minutes, filter, wash the resulting precipitate with hot water and dry.

0.18 mol (45 g) of 2-phenyl-4-benzylidene-5-oxazolinone is obtained.

Melting point: 158° C.

Step B: 2-phenylcarboxamido-3-phenylacrylic acid hydrazide

Suspend 0.08 mol (20 g) of 2-phenyl-4-benzylidene-5-oxazolinone in 125 cm$^3$ of methanol. Add 0.09 mol (5.8 g) of hydrazine hydrate. Stir for 30 minutes, filter the resulting precipitate and rinse it with ether.

0.048 mol (13.5 g) of 2-phenylcarboxamido-3-phenylacrylic acid hydrazide is obtained.

Melting point: 136° C.

Step C: 3-phenyl-5-benzyl-1,2,4-triazin-6-one

Reflux for 10 minutes 0.08 mol (22.5 g) of the compound obtained in the preceding Step dissolved in 150 ml of a molar solution of sodium hydroxide. Filter hot. Acidify the resulting precipitate and recrystallise it from ethanol. 0.048 mol (12.6 g) of 3-phenyl-5-benzyl-1,2,4-triazin-6-one is obtained.

Melting point: 183° C.

Step D
1-morpholinoethyl-3-phenyl-5-benzyl-1,2,4-triazin-6-one

The compound of the Example is obtained by operating as in Step F of Example 1 but replacing the 3-phenyl-5-isopropyl-1,2,4-triazin-6-one with the 3-phenyl-5-benzyl-1,2,4-triazin-6-one obtained in the preceding Step.

Melting point: 92° C. (base)

The compound of the Example can also be obtained using the process of Example 1, but employing phenylalanine in place of valine.

EXAMPLE 29: 1-MORPHOLINOETHYL-3-(3-CHLOROPHENYL)-5-BENZYL-1,2,4-TRIAZIN-6-ONE

By replacing the hippuric acid in Step A of Example 28 with N-(3-chlorobenzoyl)glycine, the following are obtained in succession:

STEP A: 2-(3-CHLOROPHENYL)-4-BENZYLIDENE-5-OXAZOLINONE
Melting point: 134° C.
STEP B: 2-[(3-CHLOROPHENYL)CARBOXAMIDO]-3-PHENYLACRYLIC ACID HYDRAZIDE
STEP C: 3-(3-CHLOROPHENYL)-5-BENZYL-1,2,4-TRIAZIN-6-ONE
STEP D: 1-MORPHOLINOETHYL-3-(3-CHLOROPHENYL)-5-BENZYL-1,2,4-TRIAZIN-6-ONE
Melting point: 183° C. (free base hemihydrate)

EXAMPLES 30 TO 35

By proceeding as in Example 29, using an appropriately substituted N-aroylglycine, the compounds of the following Examples are obtained:

EXAMPLE 30:
1-MORPHOLINOETHYL-3-(4-CHLOROPHENYL)-5-BENZYL-1,2,4-TRIAZIN-6-ONE

Melting point: 189° C. (acid oxalate)

EXAMPLE 31:
1-MORPHOLINOETHYL-3-(3,4-METHYLENEDIOXYPHENYL)-5-BENZYL-1,2,4-TRIAZIN-6-ONE

Melting point: 169° C. (acid oxalate)

EXAMPLE 32:
1-MORPHOLINOETHYL-3-(4-METHOXYPHENYL)-5-BENZYL-1,2,4-TRIAZIN-6-ONE

Melting point: 107° C. (base)

EXAMPLE 33:
1-MORPHOLINOETHYL-3-(4-METHYLPHENYL)-5-BENZYL-1,2,4-TRIAZIN-6-ONE

Melting point: 200° C. (acid oxalate)

EXAMPLE 34: 1-MORPHOLINOETHYL-3-(1-NAPHTHYL)-5-BENZYL-1,2,4-TRIAZIN-6-ONE

EXAMPLE 35: 1-MORPHOLINOETHYL-3-(2-PYRIMIDNYL)-5-BENZYL-1,2,4-TRIAZIN-6-ONE

EXAMPLE 36: 1-MORPHOLINOETHYL-3-PHENYL-5-(3-CHLOROBENZYL)-1,2,4-TRIAZIN-6-ONE

By replacing the benzaldehyde in Step A of Example 28 with 3-chlorobenzaldehyde, the following are obtained in the same manner:

Step A:
2-phenyl-4-(3-chlorobenzylidene)-5-oxazolinone

Melting point: 166° C.

Step B:
2-phenylcarboxamido-3-(3-chlorophenyl)acrylic acid hydrazine Melting point: 147° C.

Step C: 3-phenyl-5-(3-chlorobenzyl)-1,2,4-triazin-6-one

Melting point: 150° C.

Step D:
1-morpholinoethyl-3-phenyl-5-(3-chlorobenzyl)-1,2,4-triazin-6-one

Melting point: 187° C. (acid oxalate)

EXAMPLES 37 TO 47

The compounds of the following Examples are obtained by proceeding in the same manner as in Example 36 but using an appropriately selected aldehyde.

EXAMPLE 37:
1-MORPHOLINOETHYL-3-PHENYL-5-(2-CHLOROBENZYL)-1,2,4-TRIAZIN-6-ONE

Melting point: 197° C. (acid oxalate)

EXAMPLE 38:
1-MORPHOLINOETHYL-3-PHENYL-5-(4-CHLOROBENZYL)-1,2,4-TRIAZIN-6-ONE

Melting point: 216° C. (acid oxalate)

EXAMPLE 39:
1-MORPHOLINOETHYL-3-PHENYL-5-(4-METHOXYBENZYL)-1,2,4-TRIAZIN-6-ONE

Melting point: 200° C. (acid oxalate)

EXAMPLE 40:
1-MORPHOLINOETHYL-3-PHENYL-5-(3-BROMOBENZYL)-1,2,4-TRIAZIN-6-ONE

Melting point: 187° C. (acid oxalate)

EXAMPLE 41:
1-MORPHOLINOETHYL-3-PHENYL-5-(3,4-METHYLENE-DIOXYPHENYL)-1,2,4-TRIAZIN-6-ONE

Melting point: 151° C. (base)

EXAMPLE 42: 1-MORPHOLINOETHYL-3-PHENYL-5-[(3-INDOLYL)-METHYL]-1,2,4-TRIAZIN-6-ONE

EXAMPLE 43: 1-MORPHOLINOETHYL-3-PHENYL-5-[(3-PYRIDINYL)METHYL]-1,2,4-TRIAZIN-6-ONE

EXAMPLE 44: 1-MORPHOLINOETHYL-3-PHENYL-5-[(2-FURYL)METHYL]-1,2,4-TRIAZIN-6-ONE

EXAMPLE 45: 1-MORPHOLINOETHYL-3-PHENYL-5-(3-NITROBENZYL)-1,2,4-TRIAZIN-6-ONE

EXAMPLE 46: 1-MORPHOLINOETHYL-3-PHENYL-5-(3-HYDROXYBENZYL)-1,2,4-TRIAZIN-6-ONE

EXAMPLE 47: 1-MORPHOLINOETHYL-3-PHENYL-5-(4-METHYLBENZYL)-1,2,4-TRIAZIN-6-ONE

EXAMPLE 48: 1-(3-MORPHOLINOPROPYL)-3-PHENYL-5-(3-CHLOROBENZYL)-1,2,4-TRIAZIN-6-ONE

The product of the Example is obtained by replacing the N-(2-chloroethyl)morpholine hydrochloride in Step D of Example 36 with N-(3-chloropropyl)morpholine hydrochloride.

Melting point: 164° C. (acid oxalate)

EXAMPLE 49:
1-PYRROLIDINOETHYL-3-PHENYL-5-(3-CHLOROBENZYL)-1,2,4-TRIAZIN-6-ONE

The product of the Example is obtained by replacing the N-(2-chloroethyl)morpholine hydrochloride in Step D of Example 36 with N-(2-chloroethyl)pyrrolidine hydrochloride.

Melting point: 174° C. (acid oxalate, monohydrate)

EXAMPLE 50:
1-PYRROLIDINOETHYL-3-(3-CHLOROPHENYL)-5-BENZYL-1,2,4-TRIAZIN-6-ONE

The compound of the Example is obtained by replacing the N-(2-chloroethyl)morpholine hydrochloride in Step D of Example 29 with N-(2-chloroethyl)pyrrolidine hydrochloride.

Melting point: 188° C. (acid oxalate)

EXAMPLES 51 TO 56

By operating in the same manner as in the preceding Example, but using an appropriately selected aminoalkyl chloride hydrochloride, the following are obtained:

EXAMPLE 51: 1-(4-MORPHOLINOBUTYL)-3-(3-CHLOROPHENYL)-5-BENZYL-1,2,4-TRIAZIN-6-ONE

EXAMPLE 52: 1-DIMETHYLAMINOETHYL-3-(3-CHLOROPHENYL)-5-BENZYL-1,2,4-TRIAZIN-6-ONE

EXAMPLE 53: 1-(N-METHYLPIPERAZINOETHYL)-3-(3-CHLOROPHENYL)-5-BENZYL-1,2,4-TRIAZIN-6-ONE

EXAMPLE 54: 1-(N-PHENYLPIPERAZINOETHYL)-3-(3-CHLOROPHENYL)-5-BENZYL-1,2,4-TRIAZIN-6-ONE

EXAMPLE 55: 1-[(1-PERHYDROAZEPINYL)ETHYL]-3-(3-CHLOROPHENYL)-5-BENZYL-1,2,4-TRIAZIN-6-ONE

EXAMPLE 56: 1-PIPERIDINOETHYL-3-(3-CHLOROPHENYL)-5-BENZYL-1,2,4-TRIAZIN-6-ONE

EXAMPLE 57: 3,8-DIBENZYL-6-PHENYL-[1,2,4-TRIAZOLO][3,4-f][1,2,4]TRIAZINE

Step A: 6-chloro-5-benzyl-3-phenyl-1,2,4-triazine

Heat a solution of 15 mmol (4 g) of 3-phenyl-5-benzyl-1,2,4-triazin-6-one obtained in Step C of Example 28 in 30 ml of phosphorus oxychloride to a temperature of 80° C. After cooling, pour into iced water, render alkaline and extract with ethyl acetate. Dry the organic phase, filter, evaporate to dryness and purify by chromatography on silica (eluant ethyl acetate/hexane: 27/75)

Step B:
3,8-dibenzyl-6-phenyl-[1,2,4-triazolo]-[3,4-f][1,2,4]triazine

Heat a solution of 1.77 mmol of the compound obtained in the preceding Step and 1.5 equivalents (0.4 g) of phenylacetic acid hydrazide in 10 ml of butanol for 12 hours. After cooling, filter the precipitate and recrystallise it from ethanol.

Melting point: 165° C.

EXAMPLES 58 TO 60

The compounds of the following Examples are obtained in the same manner as in Example 57 by replacing the phenylacetic acid hydrazide in Step B with the appropriate acid hydrazide:

EXAMPLE 58:
3,6-DIPHENYL-8-BENZYL-[1,2,4-TRIAZOLO][3,4-f][1,2,4]TRIAZINE

Melting point: 190° C.

EXAMPLE 59:
3-METHYL-6-PHENYL-8-BENZYL-[1,2,4-TRIAZOLO][3,4-f][1,2,4]TRIAZINE

Melting point: 181° C.

EXAMPLE 60: 6-PHENYL -8-BENZYL-[1,2,4-TRIAZOLO][3,4-f][1,2,4]TRIAZINE

EXAMPLE 61: 3-PHENYL-5-BENZYL-6-[4-(3-CHLOROPHENYL)-1-PIPERAZINYL]-1,2,4-TRIAZINE

Suspend 2 mmol (570 mg) of 6-chloro-5-benzyl-3-phenyl-1,2,4-triazine obtained in Step A of Example 57 in 40 ml of butanol, and add 4 equivalents of 1-(3-chlorophenyl)piperazine. Heat for 12 hours at 120° C., concentrate the solution, take up in ether, filter the resulting precipitate and recrystallise it from ethanol.

Melting point: 178° C.

EXAMPLE 62:
3-PHENYL-5-BENZYL-6-(4-METHYL-PIPERAZINYL)-1,2,4-TRIAZINE

The product of the Example is obtained by proceeding as in Example 61, using N-methylpiperazine.

EXAMPLE 63:
3-PHENYL-5-BENZYL-6-DIETHYLAMINOETHYLAMINO-1,2,4-TRIAZINE

By replacing the 1-(3-chlorophenyl)piperazine in Example 61 with diethylaminoethylamine, the product of the Example is obtained in the same manner, converted into a salt by one equivalent of oxalic acid and recrystallised from isopropanol.

Melting point: 168° C. (acid oxalate)

EXAMPLES 64 TO 72

By proceeding as in Example 63, the following Examples are obtained in the same manner using appropriately substituted 6-chloro-1,2,4-triazines (intermediates in the preparation of the Examples described above) which are condensed with appropriate amines:

EXAMPLE 64:
6-[(1-ETHYL-2-PYRROLIDINYL)-METHYLAMINO]-5-BENZYL-3-PHENYL-1,2,4-TRIAZINE

Melting point: 111° C.

EXAMPLE 65:
6-PIPERIDINOETHYLAMINO-5-BENZYL-3-PHENYL-1,2,4-TRIAZINE

Melting point: 132° C.

EXAMPLE 66:
6-PIPERIDINOETHYLAMINO-5-BENZYL-3-(4-CHLOROPHENYL)-1,2,4-TRIAZINE

Melting point: 196° C. (acid oxalate)

EXAMPLE 67:
6-PIPERIDINOETHYLAMINO-5-METHYL-3-PHENYL-1,2,4-TRIAZINE

Melting point: 124° C.

EXAMPLE 68:
6-PIPERIDINOETHYLAMINO-5-ISOPROPYL-3-(4-CHLOROPHENYL)-1,2,4-TRIAZINE

Melting point: 221° C. (acid oxalate)

EXAMPLE 69:
6-PIPERIDINOETHYLAMINO-5-METHYL-3-(4-CHLOROPHENYL)-1,2,4-TRIAZINE

Melting point: 215° C. (acid oxalate)

EXAMPLE 70:
6-PIPERIDINOETHYLAMINO-3-PHENYL-1,2,4-TRIAZINE

Melting point: 105° C. (monohydrate)

EXAMPLE 71:
6-PIPERIDINOETHYLAMINO-3-PHENYL-5-(4-CHLOROBENZYL)-1,2,4-TRIAZINE

Melting point: 192° C. (acid oxalate)

EXAMPLE 72: 1-(3-PHENYL-1,2,4-TRIAZIN-6-YL)-4-[3-(4-FLUOROBENZOYL)PROPYL]-PIPERAZINE

Melting point: 155° C. (hemihydrate)

EXAMPLE 73: 6-[(3-PIPERIDINOPROPYL)AMINO]-3-(4-CHLOROPHENYL)-5-BENZYL-1,2,4-TRIAZINE

EXAMPLE 74: 6-[(4-PIPERIDINOBUTYL)AMINO]-3-(4-CHLOROPHENYL)-5-BENZYL-1,2,4-TRIAZINE

EXAMPLE 75: 6-MORPHOLINOETHYLAMINO-5-BENZYL-3-PHENYL-1,2,4-TRIAZINE

EXAMPLE 76: 6-[(1,2,5,6-TETRAHYDROPYRID-1-YL)ETHYLAMINO]-5-METHYL-3-PHENYL-1,2,4-TRIAZINE

EXAMPLE 77: 6-[(3-AZABICYCLO(3.3.0)OCT-3-YL)ETHYLAMINO]-5-BENZYL-3-PHENYL-1,2,4-TRIAZINE

EXAMPLE 78: 6-[(PERHYDROAZEPIN-1-YL)ETHYLAMINO]-5-BENZYL-3-PHENYL-1,2,4-TRIAZINE

EXAMPLE 79: 6{[3-(PERHYDROAZEPIN-1-YL)PROPYL]AMINO}-5-BENZYL-3-PHENYL-1,2,4-TRIAZINE

EXAMPLE 80: 6-{[4-(3-CHLOROPHENYL)PIPERAZIN-1-YL]ETHYLAMINO}-5-BENZYL-3-PHENYL-1,2,4-TRIAZINE

PHARMACOLOGICAL STUDY OF THE COMPOUNDS OF THE INVENTION

Example 81: Analgesic Activity Study

The activity against pain was studied in mice (20-25 g) in accordance with a protocol derived from the technique described by KOSTER (GAIRIN et al. J. Pharmacol. Exp. Ther. (1988), 245, 955). The mice, divided randomly into groups of 10, received treatment by the intraperitoneal route (excipient for the controls) 30 minutes before the intraperitoneal injection of a 1% acetic acid solution. The number of times the mice writhe between the 5th and the 20th minute after the injection is counted.

The percentage activity obtained was evaluated for each dose (% decrease in the number of times the treated mice writhe compared with the controls).

It was apparent that the compounds of the invention have a valuable analgesic activity (activity approximately 50% for certain compounds of the invention at 25 mg/kg i.p.). Furthermore, at the doses tested, the products are completely non-toxic.

EXAMPLE 82: IN VITRO STUDY OF THE AFFINITY FOR RECEPTORS OF THE CENTRAL NERVOUS SYSTEM

The in vitro affinity tests for the mu, delta, kappa, sigma, $5HT_{1A}$, $5HT_2$, $M_1$, $GABA_A$, $A_1$, and $A_2$ receptors were carried out according to conventional receptor-binding techniques.

The results of these studies show that the compounds of the invention have $K_{0.5}$ values of the order of $10^{-6}M$ with respect to sigma, M1, $A_1$, and $A_2$ receptors.

EXAMPLE 83: ACETYLCHOLINE ESTERASE-INHIBITING ACTIVITY

The dosage of the acetylcholine esterase is determined according to the colorimetric method of Ellman et al (Biochem. Pharmacol (1961), 7, 88-95). In this test, the compounds of the invention exhibit a very valuable inhibiting activity ($IC_{50}$ at $1 \times 10^{-7}$ M).

EXAMPLE 84: PHARMACEUTICAL COMPOSITION

Tablets each containing 10 mg of 1-morpholinoethyl-3-phenyl-5-isopropyl-1,2,4-triazin-6-one

| FORMULATION FOR 1000 TABLETS: | |
|---|---|
| 1-morpholinoethyl-3-phenyl-5-isopropyl-1,2,4-triazin-6-one | 10 g |
| wheat starch | 15 g |
| corn starch | 15 g |
| lactose | 65 g |
| magnesium stearate | 2 g |
| silica | 1 g |
| hydroxypropylcellulose | 2 g |

We claim:

1. A compound selected from those of formula I:

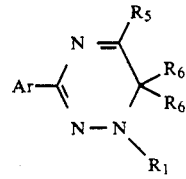

in which:

Ar represents optionally substituted aryl, pyridyl, thienyl, furyl, or pyrimidyl, $R_5$ represents hydrogen, alkyl, cycloalkyl, or cycloalkylalkyl, or aryl, or aralkyl, each of which is optionally substituted in the aromatic ring, and $R_1$ and $R_6$ together form a bond, and $R_6'$ represents a radical of the formula:

in which $R_7$ represents hydrogen or alkyl, and $R_8$ represents a group of the formula:

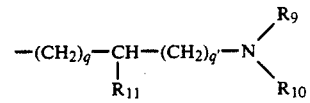

in which q represents an integer of inclusive 1 to 3, q' represents 0 or 1, $R_{11}$ represents, hydrogen or alkyl, $R_9$ and $R_{10}$ together with the nitrogen atom carrying them form a mono- or bi-cyclic heterocycle having inclusive, which from 5 to 10 atoms is saturated or contains a double bond and optionally includes in its skeleton an additional hetero atom selected from nitrogen, oxygen, and sulphur, remaining ring atoms being carbon, it being understood that, when $R_9$ and $R_{10}$ together form a heterocycle containing a second nitrogen, that nitrogen may itself be substituted by optionally substituted alkyl, aryl, or by a chain of the formula

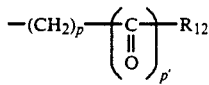

in which p represents 1, 2, or 3, p' represents 0 or 1, and R12 represents optionally substituted aryl, or R9 and R11 together with the nitrogen and carbon atoms carrying them form a heterocycle having inclusive which 5 to 7 atoms optionally includes in its skeleton an additional hetero atom selected from nitrogen, oxygen, and sulphur, remaining ring atoms being carbon, or R7 and R8 together with the nitrogen atom carrying them form a piperazine substituted at the other nitrogen by alkyl, by optionally substituted phenyl, or by a chain of the formula

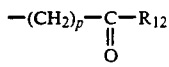

in which p and R12 are as defined above,
an optical isomer, thereof and an addition salt thereof with a pharmaceutically-acceptable acid,
it being understood that:
the term "substituted" indicates that the groups it governs may be substituted by one or more identical or different radicals selected from halogen, hydroxy, nitro, amino, trifluoromethyl, alkyl, and alkoxy, and/or may carry at two adjacent carbon atoms an $-O-(CH_2)_r-O-$ group in which r represents an integer of inclusive 1 to 3,
unless indicated otherwise, the terms "alkyl" and "alkoxy" mean such a group having inclusive, 1 to 6 carbon atoms in a straight or branched chain, and the term "cycloalkyl" means such a saturated cyclic group having 3 to 7 carbon atoms inclusive,
the term "aryl" means phenyl or naphthyl, and the term "heteroaryl" means a mono- or bi-cyclic aromatic group having inclusive, which 5 to 10 atoms includes in its carbon skeleton inclusive 1 to 3 hetero atoms selected from nitrogen, oxygen, and sulphur atoms being carbon.

2. A compound selected from those according to claim 1 corresponding to the formula:

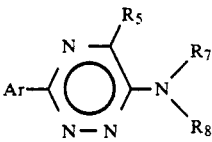

in which Ar, $R_5$, $R_7$, and $R_8$ have the meanings given in claim 1, an optical isomer, and an addition salt thereof with a pharmaceutically-acceptable acid.

3. A compound selected from those according to claim 1 corresponding to the formula:

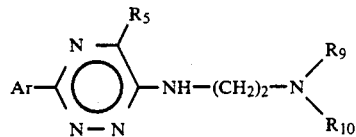

in which Ar, $R_5$, $R_9$, and $R_{10}$ have the meanings given in claim 1, an optical isomer, and an addition salt thereof with a pharmaceutically-acceptable acid.

4. A compound according to claim 1 in which $R_5$ represents hydrogen, alkyl, or aralkyl, an optical isomer, and an addition salt thereof with a pharmaceutically-acceptable acid.

5. Compound of claim 1 selected from 6-piperidinoethylamino-5-benzyl-3-phenyl-1,2,4-triazine and an addition salt thereof with a pharmaceutically-acceptable acid.

6. Compound of claim 1 selected from 6-piperidinoethylamino-5-(4-chlorobenzyl)-3-phenyl-1,2,4-triazine and an addition salt thereof with a pharmaceutically-acceptable acid.

7. Compound of claim 1 selected from 6-piperidinoethylamino-5-isopropyl-3-(4-chlorophenyl)-1,2,4-triazine and an addition salt thereof with a pharmaceutically-acceptable acid.

8. A pharmaceutical composition, useful for treating the dysfunction of sigma, $A_1$, or $A_2$ receptors, or of the cholinergic system, comprising as active principle an effective amount of a compound as claimed in claim 1 in admixture with a pharmaceutically-acceptable excipient or vehicle.

9. A method for treating a living animal afflicted with dysfunction of sigma, $A_1$, or $A_2$ receptors, or of the cholinergic system, comprising the step of administering to the said living animal an amount of a compound as claimed in claim 1 which is effective for alleviation of the said condition.

* * * * *

UNITED STATES PATENT AND TRADEMARK OFFICE
CERTIFICATE OF CORRECTION

PATENT NO. : 5,254,548

Page 1 of 2

DATED : Oct. 19, 1993

INVENTOR(S) : Camille-Georges Wermuth, Jean-Jacques Bourguignon, Isabelle Morin, Pierre Renard, Michelle Devisguet, Jean-François R. de La Faverie, Gérard Adam It is certified that error appears in the above-indentified patent and that said Letters Patent is hereby corrected as shown below:

Column 1, line 45; underline "either:"
Column 5, line 19, 20; after "formula", insert --XI--.
Column 6, line 49; underline "In vitro".
Column 6, line 53; underline "in vivo".
Column 8, approximately line 19; insert a period "." after "ture".
Column 9, line 35; move the closing parenthesis from the beginning of line 35 to the end of line 34 and insert before the hyphen.
Column 11, line 38; "MORPHOLINOETHYL-2-" should read -- MORPHOLINOETHYL-3-(2- --.
Column 13, line 30; "PYRIMIDNYL)" should read --PYRIMIDYL--.

Column 18, line 55; "of inclusive 1 to 3," should read -- of 1 to 3 inclusive, --. (Cl. 1, PA 1-4-92, P. 1)
Column 18, line 59, 60; "having inclusive, which" should read -- having 5 to 10 atoms, inclusive, which--.
Column 18, line 60; delete "from 5 to 10 atoms".
Column 19, line 9; "R12" should read -- $R_{12}$ --.
Column 19, line 11, 12; "having inclusive which 5 to 7 atoms" should read -- having 5 to 7 atoms inclusive which --.
Column 19, line 37; "of inclusive 1 to 3, " should read -- -- of 1 to 3, inclusive --.
Column 19, line 40; delete "inclusive,".
Column 19, line 41; "6 carbon atoms in" should read -- 6 carbon atoms, inclusive in --.

UNITED STATES PATENT AND TRADEMARK OFFICE
CERTIFICATE OF CORRECTION

PATENT NO. : 5,254,548
DATED : Oct. 19, 1993
INVENTOR(S) : Camille-Georges Wermuth, Jean-Jacques Bourguignon, Isabelle Morin, Pierre Renard, Michelle Devisguet, Jean-Francois R. de La Faverie, Gérard Adam It is certified that error appears in the above-indentified patent and that said Letters Patent is hereby corrected as shown below:

Column 19, approximately lines 46, 47; "having inclusive, which 5 to 10 atoms includes" should read -- having 5 to 10 atoms, inclusive, which includes --.
Column 19, line 48; "skeleton inclusive 1" should read -- -- skeleton 1 --.
Column 19, approximately line 49; "atoms selected" should read -- atoms, inclusive, selected --.
Column 19, line 50; "sulphur atoms" should read -- sulphur, remaining ring atoms --.

Signed and Sealed this

Twenty-eighth Day of June, 1994

Attest:

BRUCE LEHMAN

Attesting Officer        Commissioner of Patents and Trademarks